US008570530B2

(12) United States Patent
Liang

(10) Patent No.: US 8,570,530 B2
(45) Date of Patent: Oct. 29, 2013

(54) APPARATUS FOR DENTAL SURFACE SHAPE AND SHADE IMAGING

(75) Inventor: Rongguang Liang, Penfield, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 12/477,160

(22) Filed: Jun. 3, 2009

(65) Prior Publication Data

US 2010/0311005 A1 Dec. 9, 2010

(51) Int. Cl.
*G01B 11/24* (2006.01)
(52) U.S. Cl.
USPC ........... 356/601; 356/602; 356/613; 382/151; 382/165
(58) Field of Classification Search
USPC .................. 356/376, 364, 446, 497, 601–613; 382/151, 165
See application file for complete search history.

(56) References Cited

U.S. PATENT DOCUMENTS

| | | | |
|---|---|---|---|
| 4,641,972 A * | 2/1987 | Halioua et al. ................ | 356/604 |
| 5,372,502 A | 12/1994 | Massen et al. | |
| 5,587,832 A * | 12/1996 | Krause ........................... | 359/385 |
| 6,144,453 A | 11/2000 | Hallerman et al. | |
| 6,369,899 B1 | 4/2002 | Hamada | |
| 6,594,539 B1 | 7/2003 | Geng | |
| 6,885,464 B1 | 4/2005 | Pfeiffer et al. | |
| 7,095,503 B2 * | 8/2006 | Kim et al. ...................... | 356/497 |
| 7,098,435 B2 | 8/2006 | Mueller et al. | |
| 7,312,924 B2 | 12/2007 | Trissel | |
| RE39,978 E * | 1/2008 | Bieman ........................... | 356/604 |
| 7,317,540 B1 * | 1/2008 | Kim et al. ...................... | 356/497 |
| 7,319,529 B2 | 1/2008 | Babayoff | |
| 7,460,248 B2 * | 12/2008 | Kurtz et al. .................... | 356/521 |
| 7,988,297 B2 * | 8/2011 | Crill ............................... | 353/20 |
| 2007/0086762 A1 | 4/2007 | O'Keefe et al. | |
| 2007/0165243 A1 | 7/2007 | Kang et al. | |
| 2008/0090198 A1 | 4/2008 | Liang et al. | |
| 2010/0268069 A1 * | 10/2010 | Liang ............................ | 600/425 |

FOREIGN PATENT DOCUMENTS

EP 1 262 751 A2 12/2002
WO WO 00/08415 2/2000

OTHER PUBLICATIONS

T. Chen, H. Lensch, C. Fuchs, H. Seidel, "Polarization and Phase-Shifting for 3-D Scanning of Translucent Objects" Proceedings of IEEE Computer Society Conference on Computer Vision and Pattern Recognition (CVPR) Jun. 2007. pp. 1-8.
C. Reich, R. Ritter, J. Thesing, "3-D shape measurement of complex objects by combining photogrammetry and fringe projection"; Opt. Eng. 39(1), Jan. 2000, pp. 224-231.

(Continued)

*Primary Examiner* — Tarifur Chowdhury
*Assistant Examiner* — Isiaka Akanbi

(57) ABSTRACT

An intra-oral imaging apparatus having an illumination field generator that forms an illumination beam having a contour fringe projection pattern when receiving light from a first light source and having a substantially uniform illumination field when receiving light from a second light source. A polarizer in the path of the illumination beam has a first polarization transmission axis. A projection lens directs the polarized illumination beam toward a tooth surface and an imaging lens directs at least a portion of the light from the tooth surface along a detection path. A polarization-selective element disposed along the detection path has a second polarization transmission axis. At least one detector obtains image data from the light provided through the polarization-selective element. A control logic processor responds to programmed instructions for alternately energizing the first and second light sources in a sequence and obtaining both contour fringe projection data and color image data.

14 Claims, 14 Drawing Sheets

(56) References Cited

OTHER PUBLICATIONS

N. Birnbaum, H. Aaronson, C. Stevens, B. Cohen, "Departments Technology Integration: 3D Digital Scanners: A High-Tech Approach to More Accurate Dental Impressions" from Internet side at www.insidedentistry.net/print/hph?id=2682.

European Search Report, referring to European Patent Appln. No. 10 005 702.5, filed Jun. 1, 2010, Inventor Liang, Rongguang.

* cited by examiner

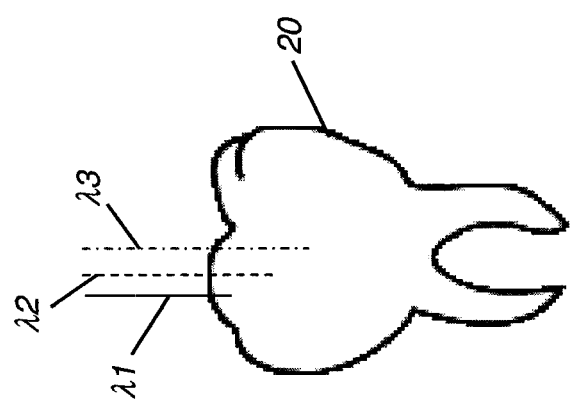
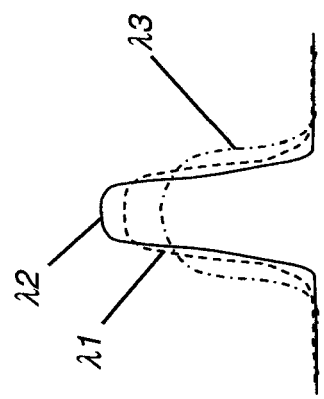
FIG. 2B
FIG. 2A

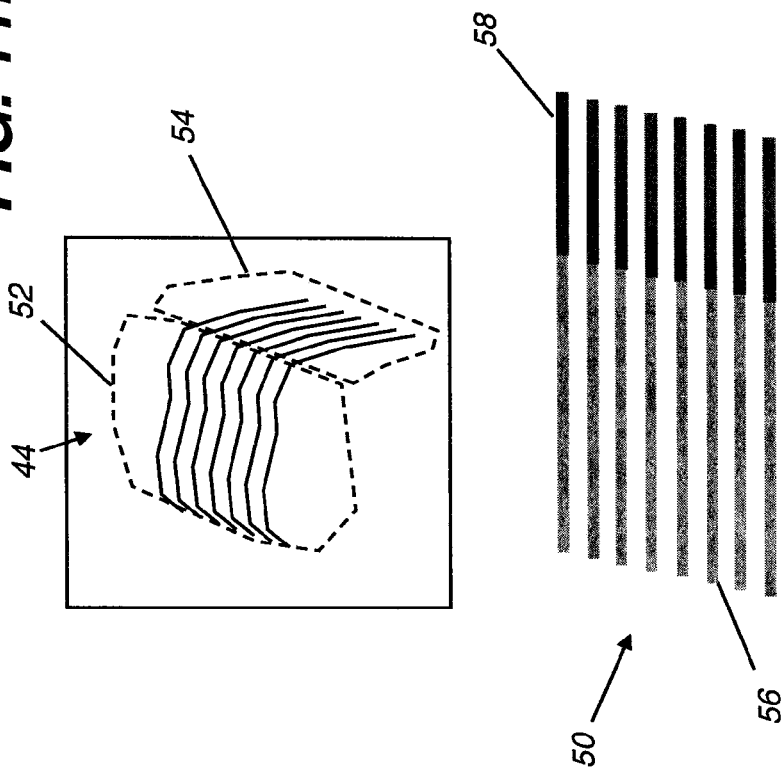
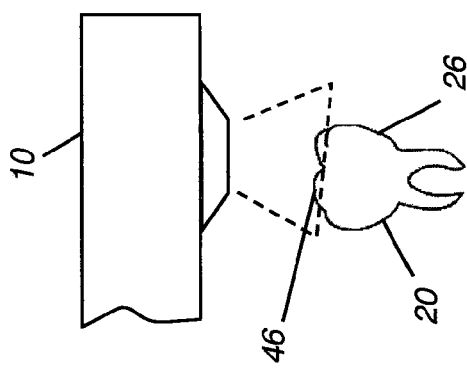

APPARATUS FOR DENTAL SURFACE SHAPE AND SHADE IMAGING

FIELD OF THE INVENTION

The invention generally relates to the field of diagnostic imaging and more particularly relates to an apparatus and method for combined three-dimensional shape and color shade imaging of the surface of teeth and other structures.

BACKGROUND OF THE INVENTION

Accurately modeling both the shape and color shade of a tooth are important functions for providing restorative dentistry and related services. Conventionally, the functions of determining tooth contour and matching tooth shade have been performed as separate operations. This makes it difficult to register or correlate the shade information to the shape information. Color shade decisions in particular are subject to human error and the overall accuracy often depends on the relative experience of the practitioner.

With the advent of digital imaging technologies, a number of tools have been made available for obtaining either surface contour data or color shade information from the tooth. One technology that has been adapted for obtaining tooth contour is fringe projection imaging. Fringe projection imaging uses patterned or structured light to obtain surface contour information for structures of various types. In fringe projection imaging, a pattern of lines of an interference fringe or grating is projected toward the surface of an object from a given direction. The projected pattern from the surface is then viewed from another direction as a contour image, taking advantage of triangulation in order to analyze surface information based on the appearance of contour lines. Phase shifting, in which the projected pattern is incrementally spatially shifted for obtaining additional measurements at the new locations, is typically applied as part of fringe projection imaging, used in order to complete the contour mapping of the surface and to increase overall resolution in the contour image.

Fringe projection imaging has been used for surface contour imaging of solid, highly opaque objects and has been used for imaging the surface contours for some portions of the human body and for obtaining detailed data about skin structure. However, a number of technical obstacles have prevented effective use of fringe projection imaging of the tooth. One challenge with dental surface imaging relates to tooth translucency. Translucent or semi-translucent materials in general are known to be particularly troublesome for fringe projection imaging. Subsurface scattering in translucent structures can reduce the overall signal-to-noise (S/N) ratio and shift the light intensity, causing inaccurate height data. Another challenge relates to high levels of reflection for various tooth surfaces. Highly reflective materials, particularly hollowed reflective structures, can effectively reduce the dynamic range of this type of imaging.

In fringe projection imaging overall, contrast is typically poor, with noise as a significant factor. To improve contrast, some fringe projection imaging systems take measures to reduce the amount of noise in the contour image. In general, for accurate surface geometry measurement using fringe imaging techniques, it is desired to obtain the light that is directly reflected from the surface of a structure under test and to reject light that is reflected from material or structures that lie beneath the surface. This is an approach for 3D surface scanning of translucent objects.

From an optics perspective, the structure of the tooth itself presents a number of additional challenges for fringe projection imaging. As noted earlier, light penetrating beneath the surface of the tooth tends to undergo significant scattering within the translucent tooth material. Moreover, reflection from opaque features beneath the tooth surface can also occur, adding noise that degrades the sensed signal and thus further complicating the task of tooth surface analysis.

One corrective measure that has been attempted to make fringe projection workable for contour imaging of the tooth is application of a coating that changes the reflective characteristics of the tooth surface itself. Here, to compensate for problems caused by the relative translucence of the tooth, a number of conventional tooth contour imaging systems apply a paint or reflective powder to the tooth surface prior to surface contour imaging. For the purposes of fringe projection imaging, this added step enhances the opacity of the tooth and reduces or eliminates the scattered light effects noted earlier. However, there are drawbacks to this type of approach. The step of applying a coating powder or liquid adds cost and time to the tooth contour imaging process. Because the thickness of the coating layer itself has a given thickness and is often non-uniform over the entire tooth surface, measurement errors readily result. No information on relative translucency of the tooth is available when the coating is applied. Further, the applied coating, while it facilitates contour imaging, can tend to mask other problems with the tooth and can thus reduce the overall amount of information that can be obtained. Even where a coating or other type of surface conditioning of the tooth is used, it can still be difficult to provide sufficient amounts of light onto, and to sense light reflected back from, all of the tooth surfaces. Different surfaces of the tooth can be oriented at 90 degrees relative to each other, making it difficult to direct enough light for accurately imaging all parts of the tooth, whether or not a coating is applied.

There have been attempts to adapt structured light surface-profiling techniques to the challenges of tooth structure imaging. For example, U.S. Pat. No. 5,372,502 entitled "Optical Probe and Method for the Three-Dimensional Surveying of Teeth" to Massen et al. describes the use of an LCD matrix to form patterns of stripes for projection onto the tooth surface. Another approach is described in U.S. Patent Application Publication 2007/0086762 entitled "Front End for 3-D Imaging Camera" by O'Keefe et al. U.S. Pat. No. 7,312,924 entitled "Polarizing Multiplexer and Methods for Intra-Oral Scanning" to Trissel describes a method for profiling the tooth surface using triangularization and polarized light, but needing application of a fluorescent coating for operation. Further, U.S. Pat. No. 6,885,464 entitled "3-D Camera for Recording Surface Structures, In Particular for Dental Purposes" to Pfeiffer et al. discloses a dental imaging apparatus using triangularization but also requiring the application of an opaque powder to the tooth surface for imaging.

The use of a powder or other surface coating, which may help facilitate contour imaging, prevents color shade information from being obtained at the same time. Thus, color shade information and surface contour information must be obtained separately, making it difficult to register the shade and shape information to each other.

An approach to obtaining both shape and shade information from one apparatus uses confocal imaging is described in U.S. Pat. No. 7,319,529 entitled "Method and Apparatus for Colour Imaging a Three-Dimensional Structure" to Babayoff. As best understood, a few hundred images of the tooth are taken, at incremental focus distances, and relative pixel intensity is used as a measure of surface contour for multiple points on the tooth surface. Color and depth data thus obtained are then combined in order to obtain and display the shape and color shade of the tooth.

While confocal imaging methods may have some advantages, there are disadvantages to using such methods. Considerable image processing resources can be required with such an approach, depending on the pixel resolution used. When this processing is done externally at a connected host computer or processor, there can be considerable overhead due to the needed volume of data transferred to the host computer or processor for confocal devices. There are also disadvantages related to optical components and design. Optical path requirements differ between what is efficient and beneficial for shape measurement and what is needed to effectively measure tooth color shade. Confocal imaging requires telecentric illumination and imaging paths, thus limiting the field of view of the imaging device.

It can be appreciated that an apparatus and method that provides both accurate surface contour imaging of the tooth and color shade data would help to speed reconstructive dentistry and could help to lower the inherent costs and inconvenience of conventional methods, such as those for obtaining a cast or other surface profile for a crown, implant, or other restorative structure.

SUMMARY OF THE INVENTION

It is an object of the present invention to advance the art of diagnostic imaging, particularly for intra-oral imaging applications. With this object in mind, the present invention provides an intra-oral imaging apparatus comprising: an illumination field generator comprising a spatial light modulator actuable to form an illumination beam having a contour fringe projection pattern when receiving incident light from a first light source and having a substantially uniform illumination field when receiving incident light from a second light source; a polarizer in the path of the illumination beam emitted from the illumination field generator and having a first polarization transmission axis; a projection lens disposed to direct the polarized illumination beam as incident illumination toward a tooth surface; an imaging lens disposed to direct at least a portion of the light reflected and scattered from the incident illumination at the tooth surface along a detection path; a polarization-selective element disposed along the detection path and having a second polarization transmission axis; at least one detector disposed along the detection path for obtaining image data from the light provided through the polarization-selective element; and a control logic processor responsive to programmed instructions for alternately energizing the first and second light sources in a sequence and obtaining both contour fringe projection data and color image data from the at least one detector.

It is a feature of the present invention that it applies light of suitable polarization and wavelength along with fringe projection patterning of varying brightness to the task of tooth contour imaging.

An advantage offered by the apparatus and method of the present invention relates to improved imaging of tooth surfaces and obtaining tooth shade information at lower cost over conventional contour imaging methods. Unlike conventional methods, no powder or other opaque substance must be applied to the tooth as a preparatory step for contour imaging.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 2A is a diagram showing wavelength-dependent penetration of illumination incident on the tooth.

FIG. 2B is a schematic diagram showing relative intensities of reflected and scattered light with different wavelengths.

FIGS. 11A-11C are schematic diagrams showing how increased brightness can be applied for improved imaging over a portion of the imaging field with contoured surfaces.

DETAILED DESCRIPTION OF THE INVENTION

Figure 1:
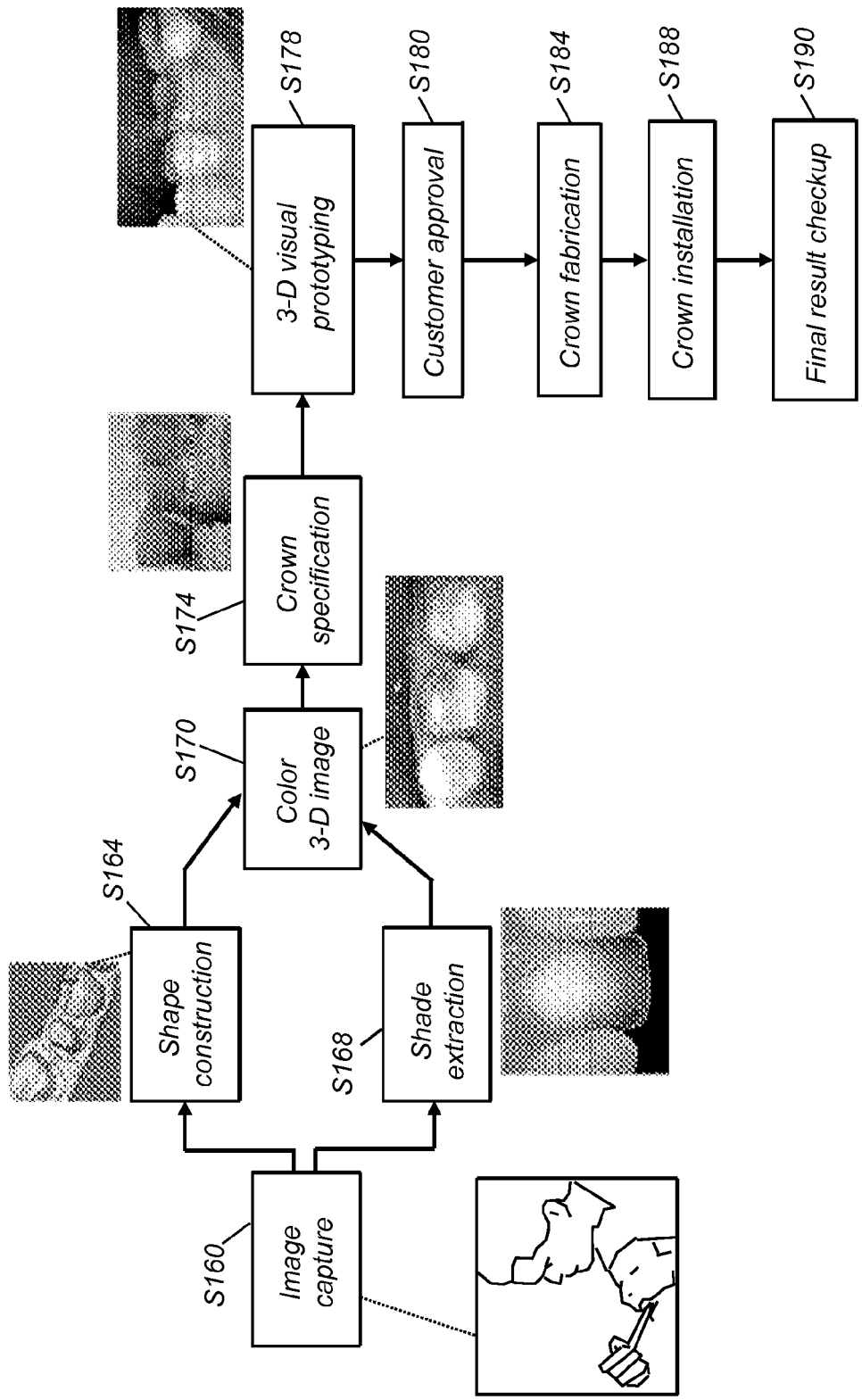
FIG. 1 is a workflow diagram showing the role of the imaging apparatus and method of the present invention in the sequence for providing a dental prosthetic appliance.

Reference is made to U.S. patent application Ser. No. 12/424,562 entitled "Dental Surface Imaging Using Polarized Fringe Projection" (Liang), filed 16 Apr. 2009, and commonly assigned.

Figures provided herein are given in order to illustrate key principles of operation and component relationships along their respective optical paths according to the present invention and are not drawn with intent to show actual size or scale. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description of the invention itself. In the drawings and text that follow, like components are designated with like reference numerals, and similar descriptions concerning components and arrangement or interaction of components already described are omitted.

In the context of the present disclosure, the term "fringe pattern illumination" is used to describe the type of structured illumination that is used for fringe projection imaging or "contour" imaging. The fringe pattern itself can include, as pattern features, multiple lines, circles, curves, or other geometric shapes that are distributed over the area that is illuminated and that have a predetermined spatial frequency, recurring at a given period.

Two portions of a line of light or other feature in a pattern of structured illumination can be considered to be substantially "dimensionally uniform" when their projected line width is the same over the length of the line to within no more than +/−15 percent. As is described in more detail subsequently, dimensional uniformity of the pattern of structured illumination is needed to maintain a uniform spatial frequency.

In the context of the present disclosure, a "substantially uniform" beam of light exhibits no visibly perceptible change in intensity over its field.

Workflow

In order to more fully appreciate the problems addressed by the present invention, it is instructive to consider how the apparatus and methods of the present invention serve the overall workflow for designing, fabricating, and installing a crown or other color-matched dental prosthesis. Referring to the workflow diagram of FIG. 1, this process begins with an image capture step S160 that obtains images used to determine the appropriate shape and shade of existing tooth structure. Fringe projection images are used to generate 3-D shape information in a shape construction step S164. Color images or monochromatic images with different illumination wavelengths are used to provide the color information needed in a shade extraction step S168. A color 3-D image generation step S170 then forms a color image using the combined shade and shape data. A prosthesis specification step S174 then uses this and other information for specifying materials and other features of the crown or other dental prosthesis. A prototyping step S178 enables visualization of the prosthetic appliance, such as on a color display for example. A customer approval step S180 follows, in which the dental practitioner approves the prototype. Once approved, a fabrication step S184 proceeds, using the shade and shape data and prototyping information generated therefrom. An installation step S188 follows in which the crown or other dental appliance is fitted to the patient and any necessary minor adjustments made. Lastly, a checkup step S190 is carried out.

For the workflow outlined in FIG. 1, the present invention concerns itself primarily with image capture step S160, shape construction step S164, shade extraction step S168, and subsequent color 3-D image generation step S170.

In general, the problem of obtaining contour information from a tooth for shape construction step S164 requires techniques and approaches that may run counter to requirements for obtaining a color image in shade extraction step S168. For example, contour imaging, because it uses a gray level output, works best with a monochrome light source, rather than with a polychromatic source; the use of a narrow band of wavelengths for the structured light pattern simplifies fringe pattern detection and inherently reduces the effects of stray ambient light, for example. For dental imaging in particular, it has been found that light of shorter wavelengths is advantaged over other light for contour imaging of the tooth because of tooth translucence and consequent scattering, which varies by wavelength. An additional difference between fringe projection imaging and color shade imaging relates to the uniformity of light intensity that is advantageous for each type, as is described in more detail subsequently.

The effect of wavelength on light scattering for the tooth is represented in the diagram of FIG. 2A and corresponding graph of FIG. 2B. FIG. 2A shows three different wavelengths $\lambda 1$, $\lambda 2$, and $\lambda 3$ as directed toward a tooth 20. The shortest wavelength at $\lambda 1$ penetrates the tooth the shortest distance. The next longest wavelength at $\lambda 2$ penetrates the tooth an additional distance. Finally, the longest wavelength at $\lambda 3$ penetrates the tooth the farthest distance. The graph of FIG. 2B shows how scattering affects the footprint of the light on the tooth surface from each wavelength. The longer the wavelength, the larger the footprint, resulting in larger measurement error. Wavelength $\lambda 1$ could be near-UV or blue light in the range of 350 to 500 nm, for example. Wavelength $\lambda 2$ could be green light in the range of 500 to 700 nm, for example. Wavelength $\lambda 3$ could be red or IR light in the range of 700 nm or higher, for example. Thus, blue or near UV light in the 350-500 nm range, because it provides the least penetration into the tooth structure, proves to be a suitable light source for fringe projection imaging in one embodiment.

Figure 3:
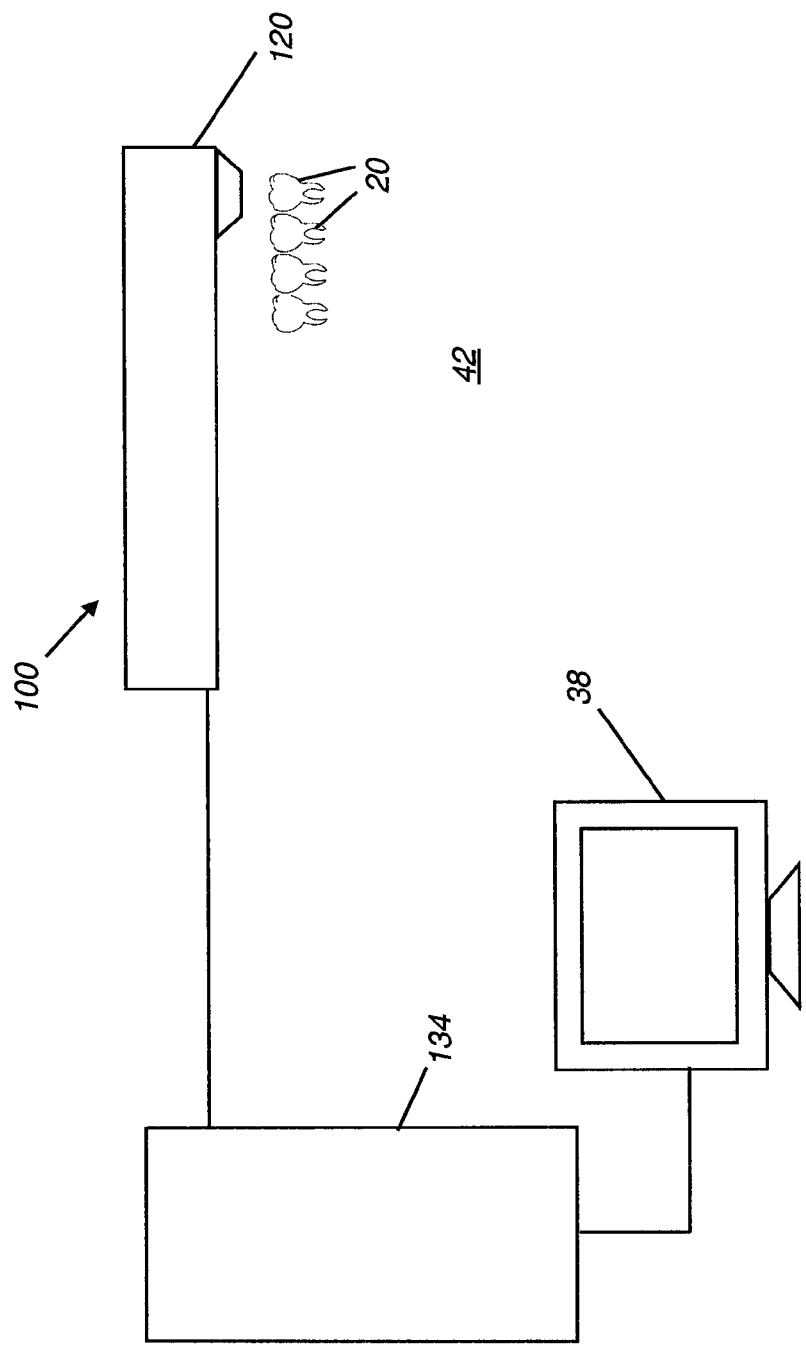
FIG. 3 is a block diagram showing components of an intra-oral imaging system according to one embodiment.

The schematic diagram of FIG. 3 shows an intra-oral imaging system 42 with an imaging apparatus 100 that has a probe 120 for forming an image of surface contour and color shade for one or more teeth 20. A host processor 134, typically a computer workstation or other dedicated logic processor, collects and processes data from imaging apparatus 100 and typically provides this information on a display 38. Handheld probe 120 can be easily positioned within the patient's mouth with little or no discomfort. Probe 120 communicates, over a wired or wireless data communication channel, with host processor 134.

Figure 4:
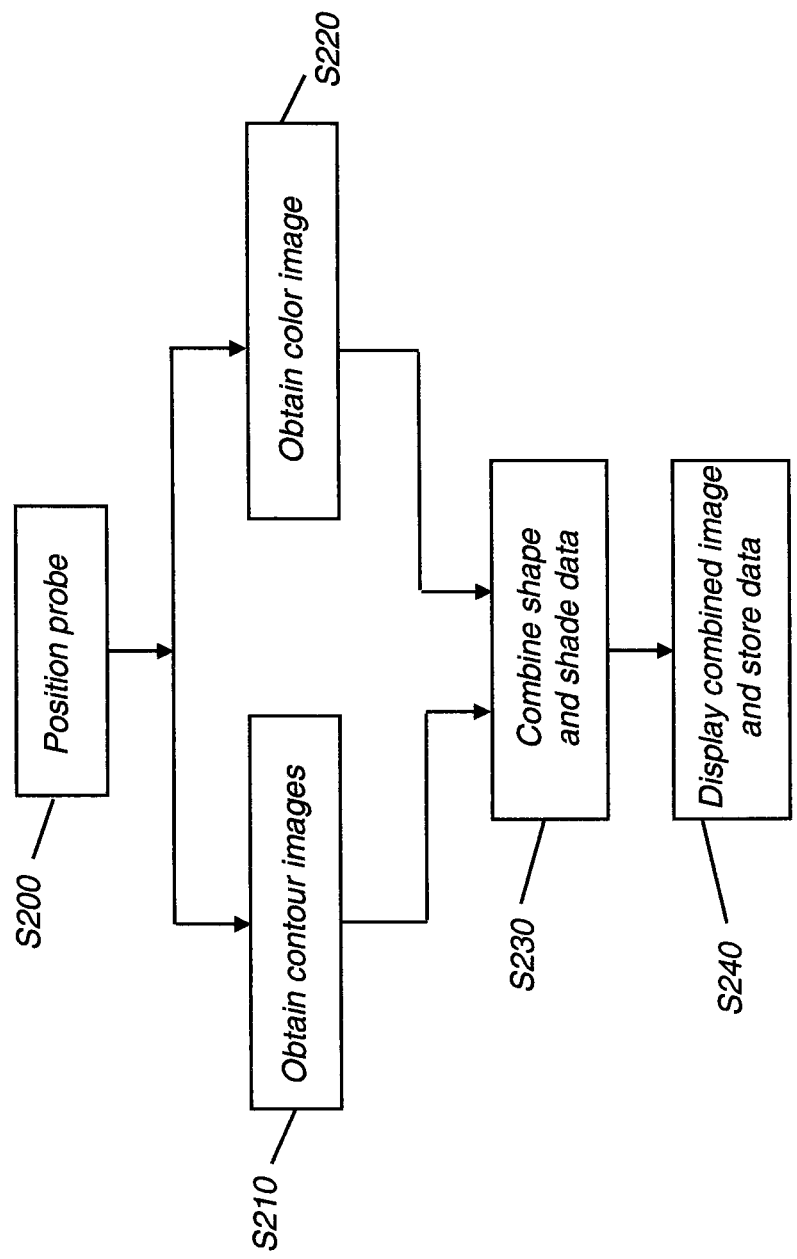
FIG. 4 is a logic flow diagram for obtaining combined shape and color shade information for a tooth or other structure.

The logic flow diagram of FIG. 4 shows the steps that are used for acquiring the combined image of surface contour and color shade in one embodiment. In a positioning step S200, the operator positions probe 120 (FIG. 3) in the mouth of the patient. A shape imaging step S210 and a shade imaging step S220 are then executed in rapid succession in order to obtain color and contour information that can be registered to each other. Registration of the two types of images to each other can use any of a number of techniques well known to those skilled in the imaging arts and may involve, for example, detection of features that are clearly pronounced or readily identifiable in each of the two types of images.

Still referring to FIG. 4, steps S210 and S220 can be executed in either order. In one embodiment, shade imaging step S220 is executed first and its results are used to condition the performance of shape imaging step S210 that immediately follows. The use of this particular type of sequence is described in more detail subsequently. In a combining step S230, the shade and shape information from the preceding steps is combined so that a single image with both contour and color shade data can be obtained, displayed, and stored in a display and store step S240.

Figure 5:
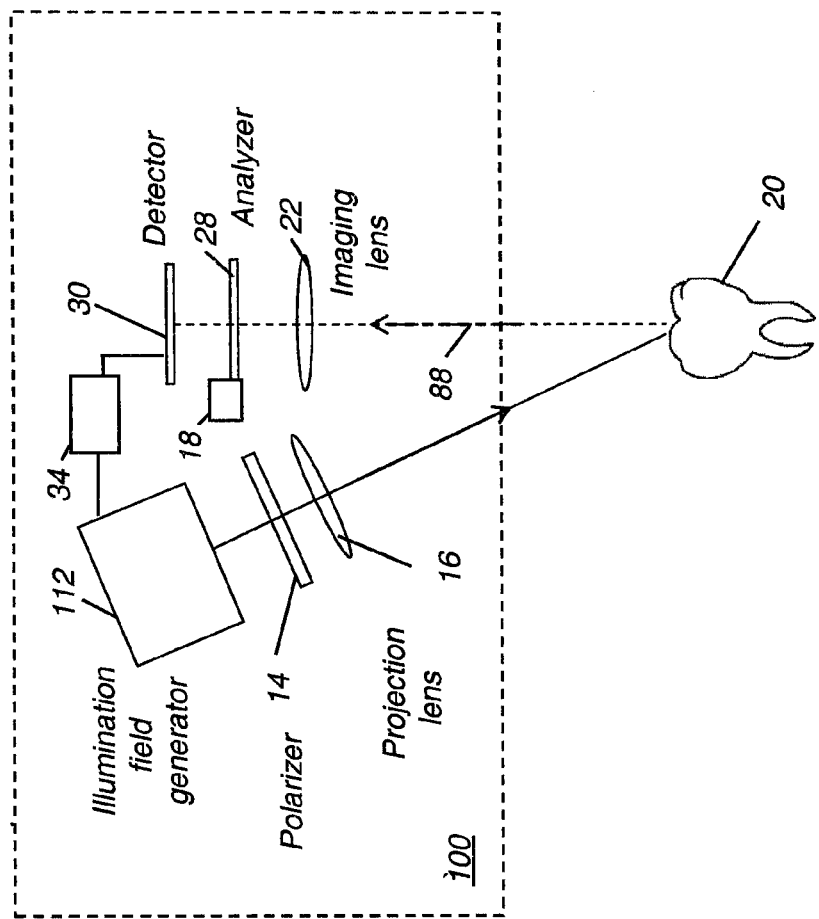
FIG. 5 is a schematic diagram of an imaging apparatus for obtaining combined shape and color shade information in one embodiment.

The schematic block diagram of FIG. 5 shows an embodiment of an imaging apparatus 100 that is configured to obtain both fringe projection and color shade images. An illumination field generator 112 is energizable to form the needed illumination for both fringe projection imaging and color imaging. For fringe projection imaging, illumination field generator 112 generates a pattern of features, which may also have variable intensity. For color imaging, illumination field generator 112 generates a substantially uniform field with broadband spectrum or, alternately, two or more sequential and uniform fields with different wavelengths. Internal components and operation of illumination field generator 112 are described in more detail subsequently.

Still referring to FIG. 5, the illumination from illumination field generator 112 is directed through a polarizer 14 and directed, as incident illumination, to tooth 20 through a projection lens 16. Light reflected and scattered from tooth 20 is provided to a detector 30, through an imaging lens 22 and a polarization-selective element such as an analyzer 28. Detector 30 is disposed along a detection path 88, at the image plane of imaging lens 22. A control logic processor 34 accepts and processes image data from detector 30 and passes the image data to host processor 134 (FIG. 3) and may use the image data to control its own operation, as described in more detail subsequently.

Fringe Projection Imaging

Imaging apparatus 100 is used to perform fringe projection imaging in step S210 (FIG. 4), just prior to or just following color imaging. Control logic processor 34 (FIG. 5) configures components of imaging apparatus 100 for this function and obtains the contour image data from the tooth at detector 30. In one embodiment, the illumination that is used for fringe projection imaging is blue light, in the 350-450 nm range.

One function of control logic processor 34 during fringe projection imaging is to incrementally shift the position of the fringe and trigger the detector to capture images that are then used to calculate three-dimensional information about the tooth surface. For the phase shifting fringe projection method, at least three images are typically needed in order to provide enough information for calculating the three-dimensional information of the object. The relative positions of the fringes for these three projected images are typically shifted by one-third of the fringe period. Control logic processor 34 can be a computer, microprocessor, or other dedicated logic processing apparatus that executes programmed instructions.

Figure 6A:
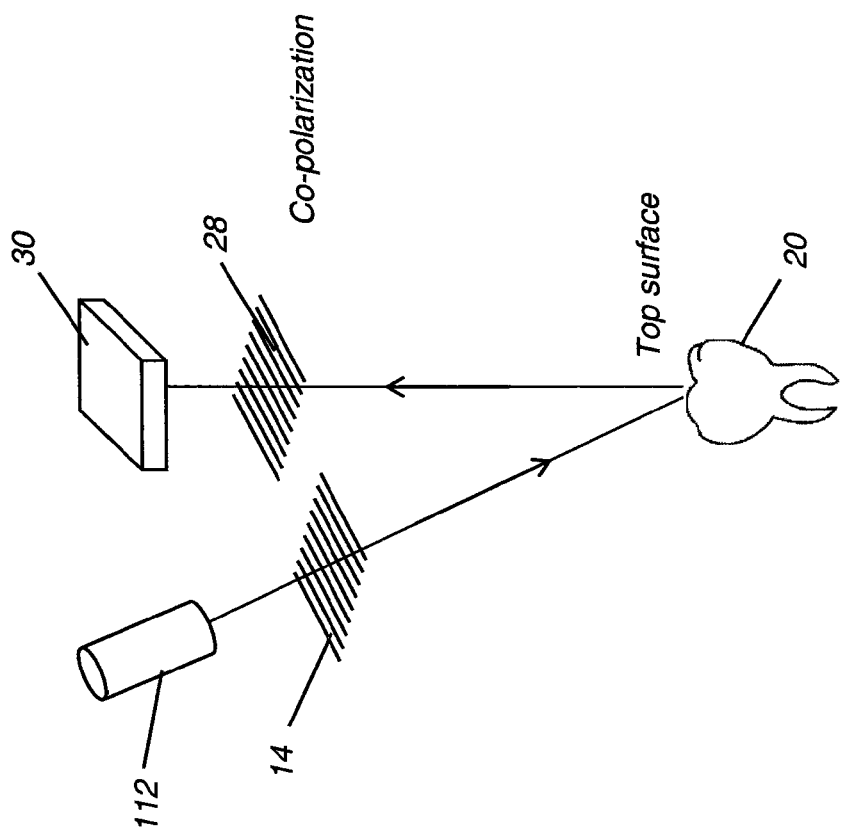
FIG. 6A is a block diagram showing the use of an analyzer with its polarization axis in parallel to the polarizer of a polarized fringe projection imaging apparatus.

Intra-oral imaging apparatus 100 of FIG. 5 uses polarized light for surface imaging of tooth 20. Polarizer 14 provides the fringe pattern illumination from illumination field generator 112 as linearly polarized light. In one embodiment, the transmission axis of analyzer 28 is parallel to the transmission axis of polarizer 14. With this arrangement, only light with the same polarization as the fringe pattern is provided to the detector 30. In another embodiment, analyzer 28, in the path of reflected light to detector 30, is rotated by an actuator 18 into either of two orientations as needed:

(a) Same polarization transmission axis as polarizer 14. In this "co-polarization" position, detector 30 obtains the specular light reflected from the surface of tooth 20, and most of the light scattered and reflected from the superficial layer of enamel surface of tooth 20, as well as some of the light scattered back from sub-surface portions of the tooth. The co-polarization orientation of the analyzer 28 axis is shown in FIG. 6A. Parallel or co-polarization provides improved contrast over other configurations.

Figure 6B:
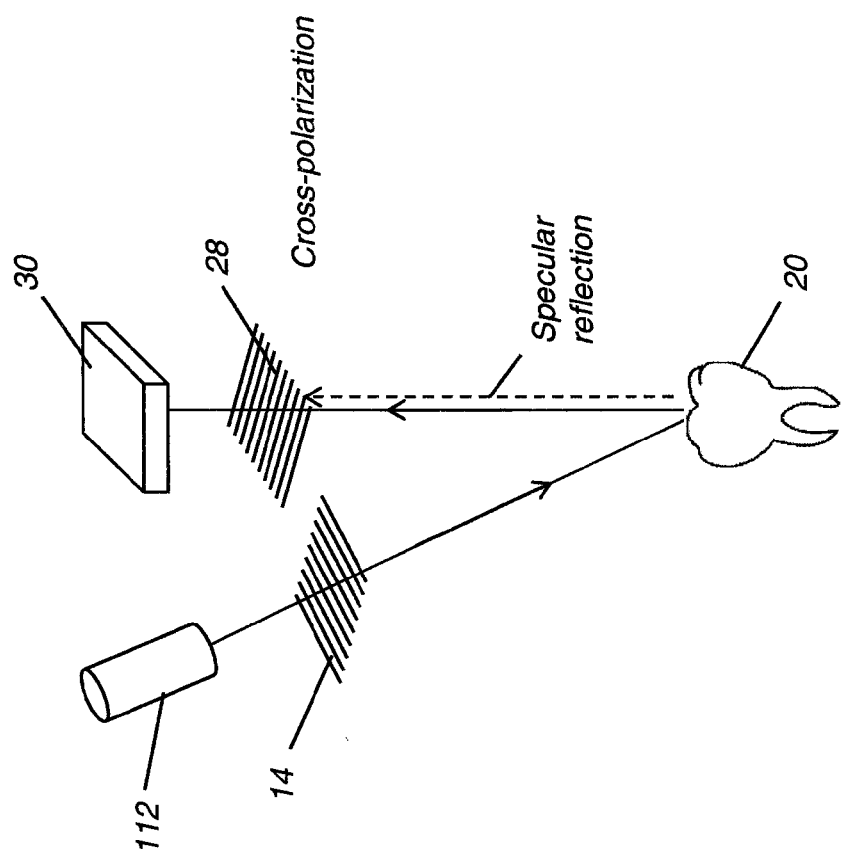
FIG. 6B is a block diagram showing the use of an analyzer with its polarization axis orthogonal to the polarizer of a polarized fringe projection imaging apparatus.

(b) Orthogonal polarization transmission axis relative to polarizer 14. Using the orthogonal polarization, or cross-polarization, helps to reduce the specular component from the tooth surface and to obtain more of the scattered light from inner portions of the tooth. The cross-polarization orientation of the analyzer 28 axis is shown in FIG. 6B.

When the tooth is imaged with an imaging system and sensor, the light that is available to the sensor can be (i) light reflected from the tooth top surface; (ii) light scattered or reflected from the near surface volume or portion of the tooth; and (iii) light scattered inside the tooth. In the context of the present disclosure, the "near-surface volume" of the tooth is that portion of the tooth structure that lies within no more than a few hundred μm of the surface.

It is known that the light reflected from the tooth surface (i), the specular light, maintains the polarization state of the incident light. As the incident light propagates further into the tooth, the light is increasingly depolarized.

Disadvantageously, some portion of the light (i) for a contour pattern may be incident on more highly reflective portions of the tooth surface, even causing some amount of saturation that degrades light detection. In contrast to conventional approaches that use all the light from the tooth, methods of the invention use at least portions of both the specular light (i) and the near-surface reflected light (ii), and avoid the light scattered deep inside the tooth (iii). It has been found that the near-surface light (ii), particularly for blue light and shorter wavelengths, is still substantially polarized. Thus, for example, a large portion of the light scattered and reflected from the superficial layer of the tooth enamel also has the same polarization state as the incident light and as the specular light (i).

Figure 7B:
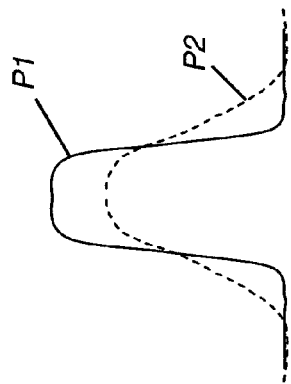
FIG. 7B is a diagram showing the relative intensities of reflected light and the scattered light from incident illumination.
Figure 7A:
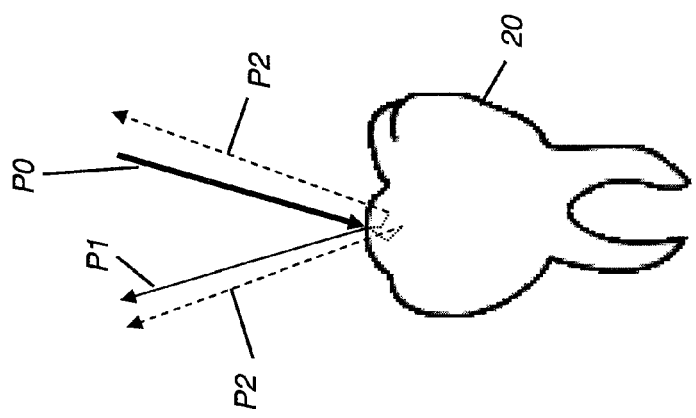
FIG. 7A is a diagram that shows the polarization-dependent reflection and scattering of illumination incident on the tooth.
Figure 8B:
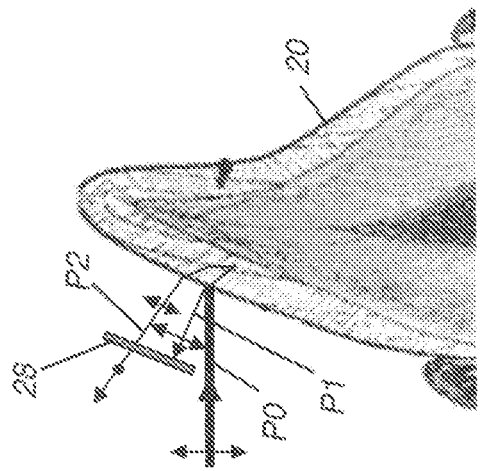
FIG. 8B shows the components of light obtained when detecting cross-polarized light.
Figure 8A:
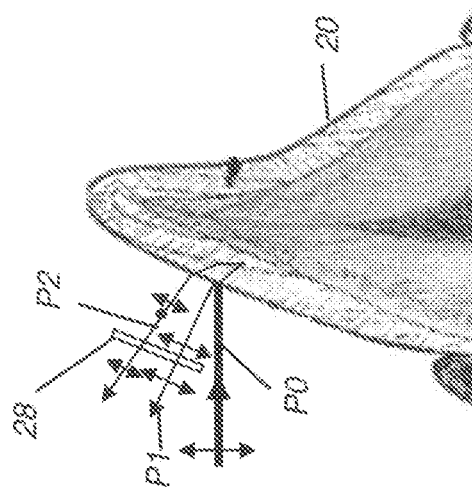
FIG. 8A shows the components of light obtained when detecting co-polarized light.

FIGS. 7A and 8A show why the apparatus and method of the present invention use scattered near-surface light from just beneath the surface of the tooth. FIGS. 8A and 8B show the difference between using the parallel polarization and cross-polarization. When a polarized light P0 with small dimension illuminates the tooth, some of the light P1 is reflected from the surface of the tooth in specular fashion and has the same polarization state as the illumination light P0. The other portion of the illumination light P0 goes into the tooth, is subject to scattering, and depolarizes. Some of the scattered light P2 escapes the tooth surface near the illumination region and can reach detector 30 (FIG. 5).

Significantly, the spatial "footprint" of the scattered light P2, which relates to the dimensions of pattern features of the structured light, such as line thicknesses, shows an increase over the corresponding spatial footprint of reflected light P1. For example, where the structured light pattern consists of parallel lines of light of a given thickness, the reflected light P1 from these pattern features has lines of substantially the same thickness as the projected pattern. However, the scattered light P2 is detected as lines of slightly increased thickness. That is, since light P2 has been scattered inside the tooth, the projected footprint on the tooth surface is broader than that of the specular reflected light, which is the same size as the illumination beam that has been projected as incident light. The graph of FIG. 7B shows the difference between the footprint of the light from the tooth surface (P1) and the light from inside the tooth (P2). To reduce the measurement error that can result, the light detected from inside the tooth should be minimized. The inventor has found that polarization provides an effective discriminator for separating the specular light (P1) from the tooth surface from the scattered light from inside the tooth, while still taking advantage of a portion of the scattered light (P2).

For the embodiment of FIG. 5, one or more spatial light modulators can be used as part of illumination field generator 112 to provide the needed shifting motion for polarized fringe projection imaging, as described in more detail subsequently. The fringe pattern itself is shifted to at least one additional alternate position during imaging, more preferably to two or more alternate positions. This shifting of the light pattern can be caused by a separate actuator (not shown in FIG. 5), such as a piezoelectric or other type of actuator that is part of illumination field generator 112 for achieving precision incremental movement. Alternately, where illumination field generator 112 uses a spatial light modulator, this shifting can be performed electronically, without mechanical movement of parts within illumination field generator 112. In addition, another actuator 18 can be positioned for providing 90 degree rotation to either polarizer 14 or analyzer 28 (such as is shown in FIG. 5) in order to obtain both co-polarization and cross-polarization images. Polarization can also be rotated to respectively orthogonal positions when using an LCD spatial light modulator.

Color Shade Imaging

Just following or just preceding fringe projection imaging, imaging apparatus 100 also obtains a color image, or a number of monochromatic images with different illumination wavelengths to form a color image, using the same optical path components described with reference to FIG. 5. Illumination field generator 112 forms a substantially uniform illumination field rather than a pattern of contour features. The light is polychromatic, from Red (from about 630-700 nm), Blue (from about 440-480 nm) and Green (from about 500-540 nm) sources. This illumination is again polarized by polarizer 14 and projected onto tooth 20. The light returned from tooth 20 is directed through analyzer 28, which can be positioned in cross-polarization orientation, that is, with its polarization transmission axis orthogonal to that of polarizer 14, as was described with reference to FIGS. 6B and 8B. This orientation is advantaged because it helps to reduce specular light which can cause saturation of the detector. Alternately, analyzer 28 can be positioned in co-polarization orientation, that is, with its polarization transmission axis parallel to that of polarizer 14, as was described with reference to FIGS. 6A and 8A.

The use of a single detector 30 as shown in the embodiment of FIG. 5 is advantaged for its low parts count and the use of the same image path and components for both fringe projection and color shade imaging. However, this embodiment can be somewhat sensitive to ambient light under some conditions.

Figure 9:
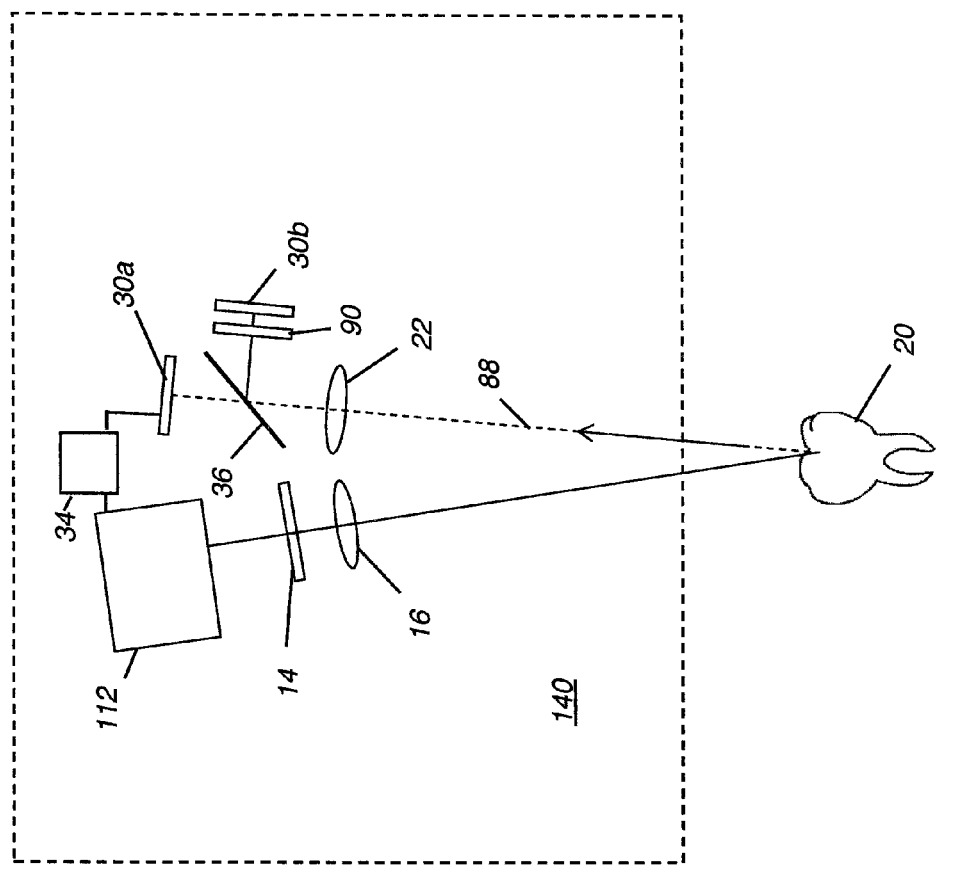
FIG. 9 is a schematic diagram of an imaging apparatus for obtaining combined shape and color shade information in an embodiment that uses multiple detectors.

The schematic block diagram of FIG. 9 shows an embodiment of an intra-oral imaging apparatus 140 that obtains both fringe projection and color images and obtains light of both polarization states without requiring rotation of either polarizer 14 or analyzer 28 between image captures. A separate analyzer is not needed. A polarization beam splitter 36 acts as the polarization-selective element in detection path 88 and separates the reflected and scattered light, reflecting the cross-polarized light to a detector 30b and transmitting the co-polarized light to a detector 30a. Because it can use light of both polarization states, intra-oral imaging apparatus 140 can obtain more information for both shape and shade measurement. A blue-transmissive filter 90 is optional and may be needed when the ambient lighting is not otherwise blocked from detection path 88. In one embodiment, filter 90 is transmissive to light in the 350-500 nm range.

Detectors 30, 30a, or 30b in the embodiments described herein can be any of a number of types of image sensing array, such as a CCD device, for example. Polarizers and analyzers can be wire-grid or other polarizer types.

Illumination Field Generator 112

Figure 10:
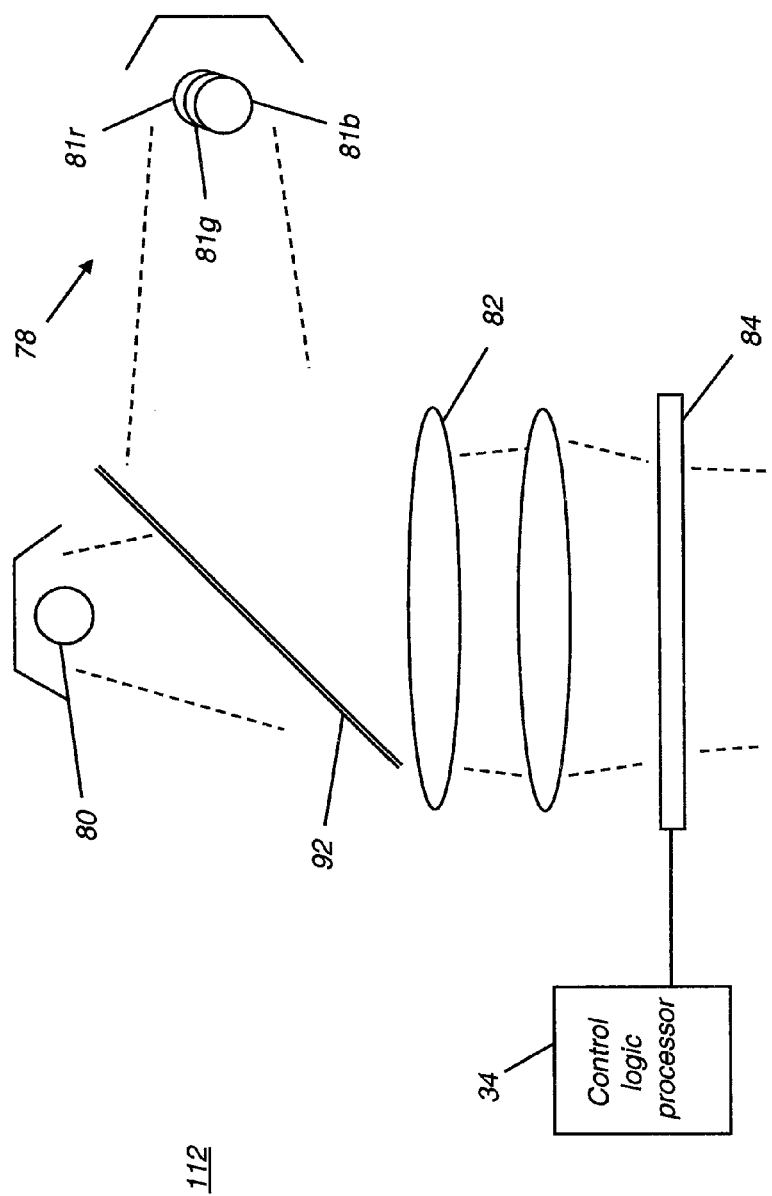
FIG. 10 is a schematic diagram showing an illumination field generator in one embodiment of the present invention.

FIG. 10 shows an embodiment of illumination field generator 112 for forming both the fringe projection pattern used for contour imaging and the uniform illumination field used for color shade imaging. In the embodiment of FIG. 10, a light source 80 is used as the light source for fringe projection imaging. A monochromatic light source 80 can be a solid-state light source, such as a Light-Emitting Diode (LED) or laser, or can be a lamp or other light source. Blue or near UV light in the 350-400 nm range is used for providing usable image content from near-surface portions of the tooth, as described earlier. A dichroic surface 92 transmits the 350-400 nm light from light source 80 to a lens or other optical element 82. A polychromatic light source 78, shown comprising light sources 81r, 81g, and 81b in the FIG. 10 embodiment, provides the needed polychromatic illumination for color shade imaging. In one embodiment, light sources 81r, 81g, and 81b are red, blue, and green LEDs, respectively, energized simultaneously or in sequence for obtaining the color images. Alternate colors, or a different number of color light sources, such as solid-state light sources with different wavelength bands, could be used in other embodiments. Alternately, a single white light source, such as a white light LED, a lamp, an Organic LED (OLED), or one or more lasers or other solid-state light emitters or other light sources could be used for providing polychromatic illumination from light source 78. Dichroic surface 92 reflects the polychromatic light from light source 78 toward optical element 82.

It should be noted that light source 80 could alternately be a broadband light source, with a filter provided in either the illumination path or along the detection path 88 or both illumination and detection paths for obtaining the fringe projection image. In an alternate embodiment, a single broadband light source is used for both fringe projection and color imaging, with a movable filter positioned in place by a motor or other actuator during fringe projection imaging and removed from the illumination path during color imaging.

Still referring to FIG. 10, a spatial light modulator 84 is provided for forming the illumination beam. In one embodiment, spatial light modulator 84 is a digital micromirror device (DMD), such as the Digital Light Processor (DLP™) from Texas Instruments, Dallas Tex., for example. A Liquid Crystal Device (LCD) or other electronically controlled light modulator could alternately be used. For fringe projection imaging, spatial light modulator 84 forms the featured fringe projection pattern of structured light using illumination from monochromatic light source 80. For color imaging, spatial light modulator 84 forms a substantially uniform field of light that is then directed to the tooth.

The spatial light modulator (SLM) offers a number of advantages for shaping the illumination beam and forming the contour fringe pattern. As one advantage, the SLM's pixel-based control of light intensity enables correction for non-uniformity of the projected beam or pattern. This capability enables the SLM to compensate for non-uniformity of the light source, such as due to aging, for example. The SLM can dynamically change the projected illumination pattern for either contour imaging or shade imaging. For example, it may be advantageous to form a patterned illumination beam for shade measurement, using the same pattern or a different pattern from that used to obtain contour data. The SLM can also be used to provide one or more lines of light or one or more point sources, which may be advantaged for translucency measurement.

Adaptive Fringe Projection Imaging

As was noted in the background material given earlier, the pronounced contours of the tooth include surfaces that are steeply sloped with respect to each other, complicating the task of directing enough light onto each surface. As a result, some surfaces of the tooth may not provide 3-D information that is sufficient. Referring to FIGS. 11A-11C, this problem is represented relative to a rear surface 26 of tooth 20. Patterned light from imaging apparatus 10 generates a contour-detecting fringe pattern 44 onto tooth 20, as shown in FIG. 11B. Fringe pattern 44 is sufficiently bright for obtaining 3-D image content over a top surface 46, as outlined over an area 52; however, the back surface area corresponding to rear surface 26 of tooth 20 and outlined as a darker area 54 is very dimly lit. This allows only a coarse estimation, at best, of the contour of rear surface 26.

In order to compensate for this lack of brightness using conventional fringe projection patterning techniques, an embodiment of the present invention selectively increases the light intensity of the projected fringe pattern illumination over a given area. In FIG. 11C, a fringe pattern 50 is shown with two different areas, differentiated by their relative light intensities. In fringe pattern 50, a first intensity 56 is provided for fringe projection imaging of surfaces such as top surface 46 that are more readily accessible for contour imaging. A second intensity 58, higher than first intensity 56 for the example shown and as indicated by darker lines in FIG. 11C, is provided for the back surface area of the tooth. It should be observed that the actual pattern feature spacing and thickness of the projected contour lines that are the pattern features in this example is not changed in this embodiment. The same spatial frequency of fringe pattern 50 is preserved. This means that the contour pattern, fringe pattern 50, remains dimensionally uniform, with individual lines or other pattern features changed only in intensity, rather than in dimension or spacing (period). Only the relative intensity of the fringe pattern illumination over one or more areas is increased where needed. For example, along any one line within structured light fringe pattern 50, there can be any number of intensities, such as the two shown as first and second intensities 56 and 58 in FIG. 11C. The line thickness within the fringe pattern does not change; the spatial frequency of the fringe pattern is preserved.

Maintaining dimensional uniformity and spatial frequency of the fringe pattern is advantageous for contour imaging because it provides a uniform resolution over the full image field. Other techniques have been proposed for changing the pattern dimensions itself, such as thickening the pattern lines over specific areas; however, because the spatial frequency of the fringe pattern changes when using such a technique, the resulting resolution of the contour image that is obtained is non-uniform. With respect to the example fringe pattern 50 given in FIG. 11C, it is instructive to observe that if the area indicated as second intensity 58 actually used thicker lines, the resulting contour image would suffer reduced resolution over this area. By maintaining the lines of fringe pattern 50 as dimensionally uniform and only increasing the intensity of light to provide second intensity 58 in this example, embodiments of the present invention provide an increased illumination without loss of resolution over the darker region.

Figure 12B:
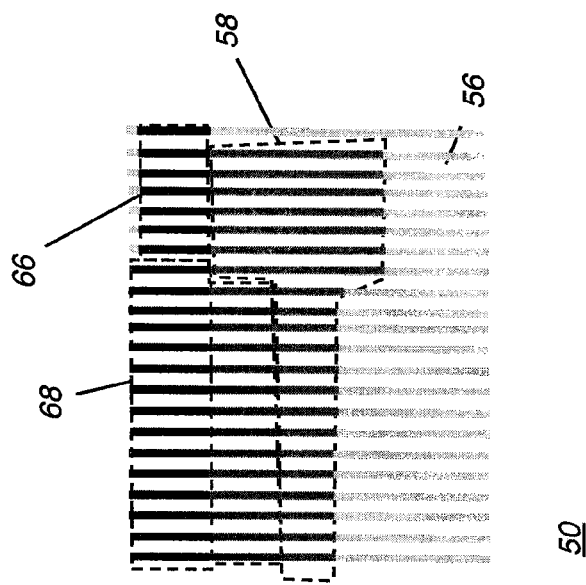
FIGS. 12A and 12B show exemplary projected light patterns generated for contour imaging in one embodiment.
Figure 12A:
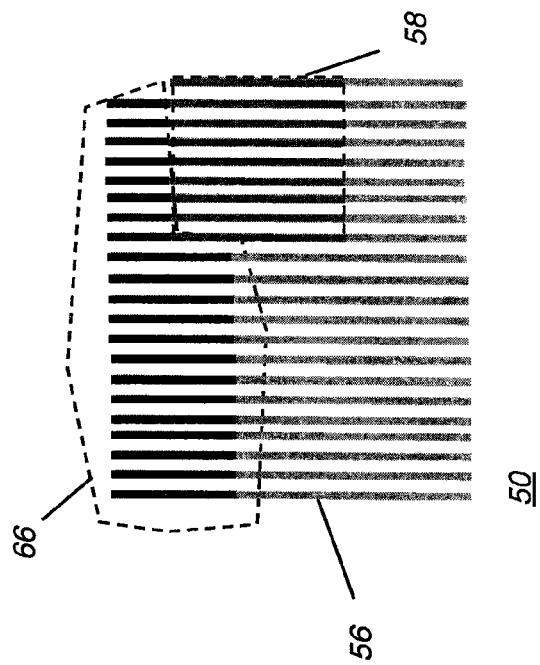

The schematic diagrams of FIGS. 11A-11C showed a simple case in which fringe pattern 50 compensates for surface steepness by using two different intensities 56 and 58. FIGS. 12A and 12B show examples of other possible arrangements that use more than two light intensities. In FIG. 12A, for example, light for the fringe pattern illumination can be of first intensity 56, second intensity 58, or a third intensity 66, represented as the highest intensity in this example. In FIG. 9B, light can be of first, second, or third intensities 56, 58, or 66 respectively, or of an even higher fourth intensity 68 as shown. The light intensity can vary along any individual pattern feature, such as along a single line in the projected fringe pattern 50.

In addition to increasing the light intensity over darker areas of the tooth surface relative to the position of imaging apparatus 10, it is also possible to reduce the light intensity over areas where there may be highly specular reflection that otherwise causes saturation of the detector. Again, it must be emphasized that what changes is the light intensity over one or more portions of the projected light pattern; line thickness and spacing, both related to the spatial frequency, remain the same for different intensities.

Referring back to the block diagrams of FIG. 5 or 9, the light intensity over the projected pattern can be changed by controlling illumination field generator 112 by means of commands from control logic processor 34, in response to programmed instructions, and by means of signals provided from control logic processor 34 to related control components. Intensity can then be increased over any portion of projected fringe pattern 50 by increasing the effective duty cycle of the rotatable mirrors of the DMD using Pulse-Width Modulation (PWM), so that the source illumination is provided for a suitable amount of time over a particular portion of the fringe pattern. Other methods of illumination intensity adjustment would apply for LCD and for other transmissive and emissive spatial light modulators, using light modulation techniques familiar to those skilled in the imaging arts.

Referring back to FIGS. 5 and 9, control logic processor 34 is programmed with instructions that automatically adapt the local intensities of lines or other features in fringe pattern 50 according to imaging conditions. In one embodiment, color imaging of the tooth is performed first, and the color image analyzed to determine which portions of the illumination to intensify. In another embodiment, an initial fringe projection image is captured and checked to determine areas for increasing or decreasing intensity for obtaining the contour image. Then, the actual contour image is captured using this information.

Figure 13:
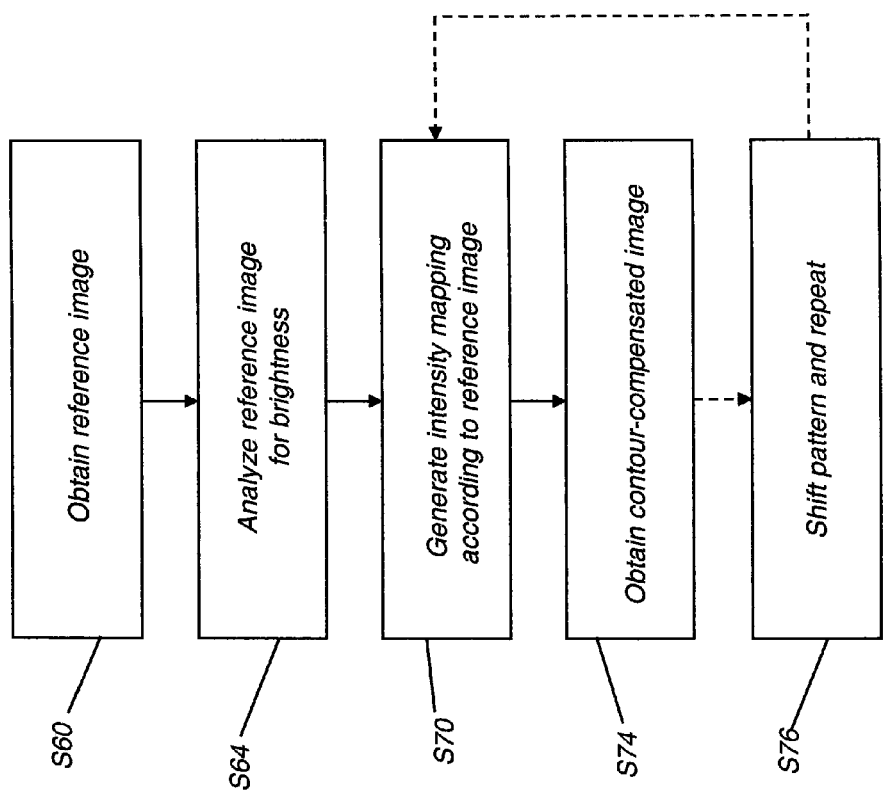
FIG. 13 is a logic flow diagram that shows the sequence for obtaining a contour-compensated image.

The logic flow diagram of FIG. 13 shows a sequence of steps that are used for adaptive fringe projection imaging in one embodiment. In an initial step S60 a first reference image is obtained. The reference image can be a contour image, formed by projecting structured light onto the tooth surface. Alternately, the reference image can be a conventional two-dimensional image obtained from projection of a uniform field of light onto the tooth surface. The reference image that is obtained can be at full resolution; alternately, since the reference image is not used directly for imaging but instead to determine the overall amount of light that is returned over each surface area, the reference image can be at lower resolution.

Still referring to FIG. 13, an analysis step S64 follows, in which areas from the sensed reference image that are not sufficiently bright are identified. For dental imaging applications, analysis step S64 can take advantage of known data about tooth structure. The operator, for example, may identify the tooth by number or provide other information that is used in analysis step S64. A map generation step S70 is then executed, in which areas of greater or lesser intensity are defined according to the first reference image. With respect to FIGS. 12A and 12B, step S70 then sets up variable intensity fringe pattern 50. An image acquisition step S74 then uses the generated fringe pattern 50 for obtaining a contour image with added brightness as described with respect to FIGS. 11A-11C. Image acquisition step S74 may be followed by an optional looping step S76 that repeats the analysis of map generation step S70 in order to generate a second or other additional mappings so that the projected structured illumination pattern can be shifted, with appropriate changes in intensity, one or more times. This shifting is done in order to obtain a more accurate evaluation of tooth contour using fringe projection techniques. The individually obtained contour images are combined to obtain surface structure information, using techniques well known in the imaging arts. In one embodiment, image acquisition step S74 also includes energizing actuator 18 (FIG. 5) in order to obtain images using both co-polarization (as in FIG. 6A) and cross-polarization (FIG. 6B).

It should be noted that, in an alternate embodiment, the thickness of contour fringe pattern lines or the relative size of other pattern elements could be changed to provide additional light, or to reduce light, over portions of the tooth. However, contour imaging data would be at reduced resolution and shape computation processing more complex.

Embodiments of the present invention provide both color imaging and improved contour imaging for teeth by taking advantage of properties of light and capabilities of spatial light modulators for forming an adaptive fringe projection pattern. The use of a spatial light modulator enables a fringe pattern of variable intensity to be formed, as well as a uniform illumination field for color imaging. The separate fringe projection and color images can be taken in rapid succession, minimizing problems with registering the shape and shade content in order to provide an accurate color 3-D image of the tooth or other structure. The apparatus and methods of the present invention compensate for problems related to the translucence of the tooth by using short-wavelength light for fringe projection imaging and by employing principles of polarized light for both fringe projection and color imaging.

As described earlier with respect to FIG. 1, the image data obtained using the apparatus and methods of the present invention can be used for improving the accuracy and timeliness of fabrication for crowns and other dental prosthetics. This can help to reduce or eliminate the need for obtaining impressions under some conditions, reducing the overall expense of dental care. Thus, the imaging performed using this method and apparatus can help to achieve superior-fitting prosthetic devices that install with little or no adjustment by the dentist. From another aspect, the apparatus and method of the present invention can be used for long-term tracking of tooth, support structure, and bite conditions, helping to diagnose and prevent more serious health problems. Overall, the data generated using this system can be used to help improve communication between patient and dentist and between the dentist, staff, and lab facilities.

Advantageously, the apparatus and method of the present invention provide an intra-oral imaging system for 3-D imaging of teeth and other dental features without requiring the use of a special powder or application of some other temporary coating for the tooth surface. The system offers high resolution, in the 25-50 µm range in one embodiment.

The invention has been described in detail with particular reference to a presently preferred embodiment, but it will be understood that variations and modifications can be effected within the spirit and scope of the invention. For example, any of a number of different types of spatial light modulator could be used as part of the illumination field generator. Lenses 16 and 22, shown as single components in various schematic diagrams, could be more complex arrangements with one or more refractive or reflective elements. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

10. Imaging Apparatus
14. Polarizer
16. Lens
18. Actuator
20. Tooth
22. Lens
26. Rear surface
28. Analyzer
30, 30$a$, 30$b$. Detector
34. Control logic processor
36. Polarization beam splitter
38. Display
42. Intra-oral imaging system
44. Pattern
46. Top surface
50. Fringe pattern
52, 54. Area
56. First intensity
58. Second intensity
S60. Initial step
S64. Analysis step
66. Third intensity
68. Fourth intensity
S70. Map generation step
S74. Image acquisition step
S76. Looping step
78, 80. Light source
81$r$, 81$g$, 81$b$. Light source
82. Optical element
84. Spatial light modulator
88. Detection path
90. Filter
92. Dichroic surface
100. Imaging apparatus
112. Illumination field generator
120. Probe
134. Host processor
140. Imaging apparatus
S160. Image capture step
S164. Shape construction step
S168. Shade extraction step
S170. Color 3-D image generation step
S174. Prosthesis specification step
S178. Prototyping step
S180. Approval step
S184. Fabrication step
S188. Installation step
S190. Checkup step
S200. Positioning step
S210. Shape imaging step
S220. Shade imaging step
S230. Combining step
S240. Display and store step
B. Box
P0, P1, P2. Polarized light
$\lambda 1, \lambda 2, \lambda 3$. Wavelength

What is claimed is:

1. An intra-oral imaging apparatus comprising:
   an illumination field generator comprising:
      a first light source for providing monochromatic light,
      a second light source for providing polychromatic light, and
      a spatial light modulator actuable to form an first illumination beam having a contour fringe projection pattern when receiving incident light from the first light source and to form a second illumination beam having a substantially uniform illumination field when receiving incident light from the second light source;
   a polarizer in a path of the illumination beams emitted from the illumination field generator and having a first polarization transmission axis;

a projection lens disposed to direct the illumination beams that are polarized by the polarizer as incident illumination toward a tooth surface;

an imaging lens disposed to direct at least a portion of light reflected and scattered from the incident illumination at the tooth surface along a detection path;

a polarization-selective element disposed along the detection path and having a second polarization transmission axis;

at least one detector disposed along the detection path for obtaining image data from the light provided through the polarization-selective element; and a control logic processor responsive to programmed instructions for alternately energizing the first and second light sources in a sequence and obtaining both contour fringe projection data and color image data from the at least one detector and registering the contour fringe projection data and color image data for display as a color three-dimensional image.

2. The imaging apparatus of claim 1 further comprising an actuator coupled to either the polarizer or the polarization-selective element and energizable to rotate the coupled polarizer or polarization-selective element to one of two respectively orthogonal positions.

3. The imaging apparatus of claim 1 wherein the polarization-selective element is an analyzer.

4. The imaging apparatus of claim 1 wherein the polarization-selective element is a polarization beam splitter and wherein the at least one detector comprises a first detector disposed to receive light transmitted through the polarization beam splitter and further comprises a second detector disposed to receive light reflected from the polarization beam splitter.

5. The imaging apparatus of claim 1 wherein the spatial light modulator is taken from the group consisting of a digital micromirror device and a liquid crystal device.

6. The imaging apparatus of claim 1 wherein at least one of the first and second light sources comprises a light-emitting diode.

7. The imaging apparatus of claim 1 wherein the second light source comprises a plurality of solid-state light sources.

8. The imaging apparatus of claim 1 further comprising a filter disposed along the detection path and transmissive to light in the 350-500 nm range.

9. A method for intra-oral imaging comprising:

forming an illumination beam having a contour fringe projection pattern when emitting light from a first light source that provides monochromatic light and having a uniform illumination field when emitting light from a second light source that provides polychromatic light;

polarizing the illumination beam along a first polarization transmission axis;

directing the polarized illumination beam as incident illumination toward a tooth surface;

directing at least a portion of the light reflected and scattered at the tooth surface from the incident illumination along a detection path;

disposing a polarization-selective element along the detection path having a second polarization transmission axis;

alternately energizing the first and second light sources in a sequence and obtaining both contour fringe projection image data and color image data from the light that is provided through the polarization-selective element; and registering the contour fringe projection image data and color image data for display as a color three-dimensional image.

10. The method of claim 9 wherein the first light source emits light in the range from 350-500 nm.

11. The method of claim 9 wherein forming the illumination beam comprises energizing a spatial light modulator.

12. The method of claim 9 wherein forming the illumination beam having the contour fringe projection pattern further comprises increasing the intensity of one or more portions of the fringe projection pattern corresponding to the tooth surface.

13. The method of claim 12 wherein increasing the intensity preserves the spatial frequency of the fringe projection pattern.

14. The method of claim 9 wherein emitting light from the second light source comprises emitting light from each of two or more solid-state light sources in succession, wherein the solid-state light sources emit light of different wavelength bands.

* * * * *